(12) United States Patent
Brinz et al.

(10) Patent No.: US 8,000,515 B2
(45) Date of Patent: Aug. 16, 2011

(54) AUTOMATIC DETECTION OF COATING FLAWS

(75) Inventors: Thomas Brinz, Bissengen A.D. Teck (DE); Jane Lewis, Bristol (GB); Markus Tiefenbacher, Fellbach-Schmiden (DE); Thomas Geiger, Walddorfhaeslach (DE); Tobias Burk, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 952 days.

(21) Appl. No.: 11/901,638

(22) Filed: Sep. 17, 2007

(65) Prior Publication Data

US 2008/0075329 A1  Mar. 27, 2008

(30) Foreign Application Priority Data

Sep. 21, 2006  (DE) .......... 10 2006 044 443

(51) Int. Cl.
*G06K 9/00* (2006.01)

(52) U.S. Cl. .......... 382/141; 250/306; 348/86; 348/125; 700/108; 438/16; 702/35; 356/237.1; 356/426

(58) Field of Classification Search .......... 382/141–152; 250/306–311; 348/86–95, 125–134; 700/95–212; 29/833; 438/16; 356/237.1–237.6, 426–431; 702/35–40
See application file for complete search history.

(56) References Cited

U.S. PATENT DOCUMENTS

| | | | |
|---|---|---|---|
| 5,331,169 A | | 7/1994 | Tanaka et al. |
| 5,347,128 A | | 9/1994 | Puram et al. |
| 6,367,968 B1 * | | 4/2002 | Ringermacher et al. .......... 374/7 |
| 6,367,969 B1 * | | 4/2002 | Ringermacher et al. .......... 374/7 |
| 6,394,646 B1 * | | 5/2002 | Ringermacher et al. .......... 374/7 |
| 6,517,236 B2 * | | 2/2003 | Sun et al. .......... 374/4 |
| 6,542,849 B2 * | | 4/2003 | Sun .......... 702/172 |
| 6,830,863 B2 * | | 12/2004 | Wachi et al. .......... 430/200 |
| 7,199,367 B2 * | | 4/2007 | Favro et al. .......... 250/341.6 |
| 7,362,973 B1 * | | 4/2008 | Dickson et al. .......... 398/40 |
| 7,365,330 B1 * | | 4/2008 | Sun .......... 250/341.6 |
| 7,409,313 B2 * | | 8/2008 | Ringermacher et al. .......... 702/172 |
| 7,419,298 B2 * | | 9/2008 | Ouyang et al. .......... 374/5 |
| 7,538,938 B2 * | | 5/2009 | Sun .......... 359/359 |
| 7,605,924 B2 * | | 10/2009 | Howard et al. .......... 356/502 |
| 7,899,325 B2 * | | 3/2011 | Dickson et al. .......... 398/40 |
| 2003/0193987 A1 * | | 10/2003 | Zalameda et al. .......... 374/5 |
| 2005/0167596 A1 * | | 8/2005 | Rothenfusser et al. .... 250/341.6 |
| 2005/0263706 A1 | | 12/2005 | Park et al. |
| 2007/0036199 A1 * | | 2/2007 | Ouyang et al. .......... 374/120 |
| 2007/0143061 A1 * | | 6/2007 | Ringermacher et al. .......... 702/136 |
| 2007/0285766 A1 * | | 12/2007 | Sun .......... 359/361 |
| 2007/0299628 A1 * | | 12/2007 | Sun .......... 702/170 |
| 2008/0075329 A1 * | | 3/2008 | Brinz et al. .......... 382/108 |
| 2008/0173078 A1 * | | 7/2008 | Christ et al. .......... 73/104 |
| 2009/0219970 A1 * | | 9/2009 | Hollander et al. .......... 374/121 |

FOREIGN PATENT DOCUMENTS

| | | |
|---|---|---|
| EP | 0461780 | 12/1991 |
| EP | 1726943 | 11/2006 |
| GB | 2 164 147 | 3/1986 |
| GB | 2220065 | 12/1989 |
| JP | 62198708 | 9/1987 |
| JP | 4248451 | 9/1992 |
| JP | 6215755 | 8/1994 |

* cited by examiner

*Primary Examiner* — Aaron W Carter

(74) *Attorney, Agent, or Firm* — Kenyon & Kenyon LLP

(57) ABSTRACT

A method and a device for inspecting surface coatings on workpieces, in particular of lacquer coatings, using an image capture and/or image processing system. The image capture and/or image processing system is designed to measure and/or process electromagnetic radiation from surface coating and/or a layer beneath it which is at least partially outside of the visible wavelength range.

12 Claims, 2 Drawing Sheets

AUTOMATIC DETECTION OF COATING FLAWS

FIELD OF THE INVENTION

The present invention relates to a device and a method for inspecting surface coatings on workpieces, in particular of lacquer coatings.

BACKGROUND INFORMATION

Various workpieces are provided with a surface coating in order to protect their surface and/or to superpose particular properties. In addition to forming a coating that is as homogeneous as possible, a proper functioning of this protective coating requires that it bonds well to the workpiece to be coated. If this is not the case, then the intended protective effect can be in part considerably impaired or disturbed. Other disturbing factors may be due to damage to the surface of the workpiece to be coated and/or to irregularities in the protective coating to be applied.

Such disturbances or flaws in the coating may be e.g. blistering, craters, popping, dirt, wetting disturbances, spreading disturbances or the like.

For the purpose of inspecting coatings, visual assessments of the coated surfaces are possible and known, in part using appropriate technical aides such as the use of a microscope or the like. Automating the detection of flaws with the aid of a camera and an image evaluation is in part massively impeded by exposure and/or reflection problems with respect to the different reflective properties of different coating materials or even of the colors of similar coating materials. Thus, for example, an automatic coating inspection of clear lacquers, black-pigmented lacquers and very highly glossy lacquers is not possible due to an insufficient level of contrast.

SUMMARY OF THE INVENTION

The present invention is therefore based on the objective of providing an improved option for automatically detecting coating flaws.

Accordingly, the present invention relates to a device for inspecting surface coatings on workpieces, in particular of lacquer coatings, using an image capture and image processing system. It is distinguished by the fact that the image capture and/or image processing system is designed to measure and/or process electromagnetic radiation from a surface coating and/or from a layer beneath it which is at least partly outside of the visible wavelength range.

Such a device has the advantage that optical reflections in the range of the visible wavelengths cannot interfere with the evaluation of the images captured by the image capture system. On the other hand, the installation of hitherto required special lighting devices may even be completely omitted.

In particular, it is seen as advantageous in this connection if the image capture and/or processing system is designed to work in the infrared and/or ultraviolet wavelength range.

The use of an image capture and/or processing system operating in the infrared wavelength range makes it possible e.g. advantageously to measure and evaluate, in the form of a thermal image, the thermal conductivity and/or the thermal capacity of the surface coating and/or of a layer beneath it of the coating of a workpiece to be inspected. Optical radiation and emissions in the visible range play no role at all in this measurement since they have no interfering effects that could influence the measuring method on account of the fact that the two wavelength ranges are completely separate from each other.

The present invention is therefore based on the realization of measuring and evaluating these various radiation and emission properties of a protective coating and, if applicable, also those of an underlying layer in a selective manner for particular wavelength ranges.

Such a device is e.g. particularly suitable for detecting flaws that extend directly to the substrate or workpiece to be covered by the coating. For detecting such flaws it is particularly advantageous if a predominantly perpendicular alignment is provided between an infrared camera and the coating to be inspected.

Additionally, an isothermal fixation of the text specimen is seen as advantageous since this facilitates an evaluation of local and/or regional differences of radiation properties of the test specimen.

The different degrees of emission of different materials, which are thus measurable, accordingly result in different signals when measuring the infrared intensity. In those places where the substrate e.g. is not covered by lacquer, such as e.g. in the case of scratches, wetting disturbances or the like, the device measures the emission intensity of the substrate, whereas in coated areas the emission of the coating is measured. This device is therefore suitable for measuring all damages in which the damage extends all the way to the substrate or the coated workpiece, or in which the damage causes a change in the degrees of emission.

To detect damages that do not extend to the substrate or workpiece, such as e.g. blisters in the protective coating or dirt and the like, another specific embodiment may provide for the image capture and/or processing system to be configured to detect a change in the thermal conductivity and/or the thermal capacity of the surface coating and/or of a layer beneath it.

For this purpose, e.g. building on the already mentioned isothermal fixation of the coated substrate or workpiece, which may be implemented, for example, in cooperation with a device for applying a constant temperature to the workpiece, it is possible to provide an additional device for introducing a local temperature difference. For example, this may be the introduction of a preferably locally limited heat or cold pulse. To this end, e.g. a coolant spray may be used. This differential temperature input initially effects a local and in the further course a regional change of the thermal radiation of the test specimen to be measured and evaluated by the device. In the regions in which there are coating damages or flaws, the propagation rate in the temperature change corresponding to the respective vicinity is substantially disturbed and a coating flaw thus becomes detectable.

Another advantage of this device lies in the fact that the surface coating may be inspected already in its not yet cured state, that is, basically directly following the coating process, e.g. in a painting line. Depending on the cause, detected lacquer flaws may thus possibly be remedied in a second, directly subsequent coating process in the problem region, without having to take the substrate or workpiece out of the manufacturing process.

In this connection, it would furthermore also be conceivable to provide a marking device for marking the specified flaw location, which can be treated in a subsequent process step in a manner appropriate to its cause and possibly be corrected in the same or in another, subsequent process step.

Furthermore, the present invention also relates to a corresponding method for inspecting surface coatings on workpieces, in particular of lacquer coatings, using an image capture and/or image processing system. This is distinguished by the fact that the image capture and/or image processing system detects and/or processes electromagnetic radiation or emission properties of the surface coating and/or of a layer beneath it which lie at least partially outside of the visible wavelength range.

DETAILED DESCRIPTION

Figure 1:
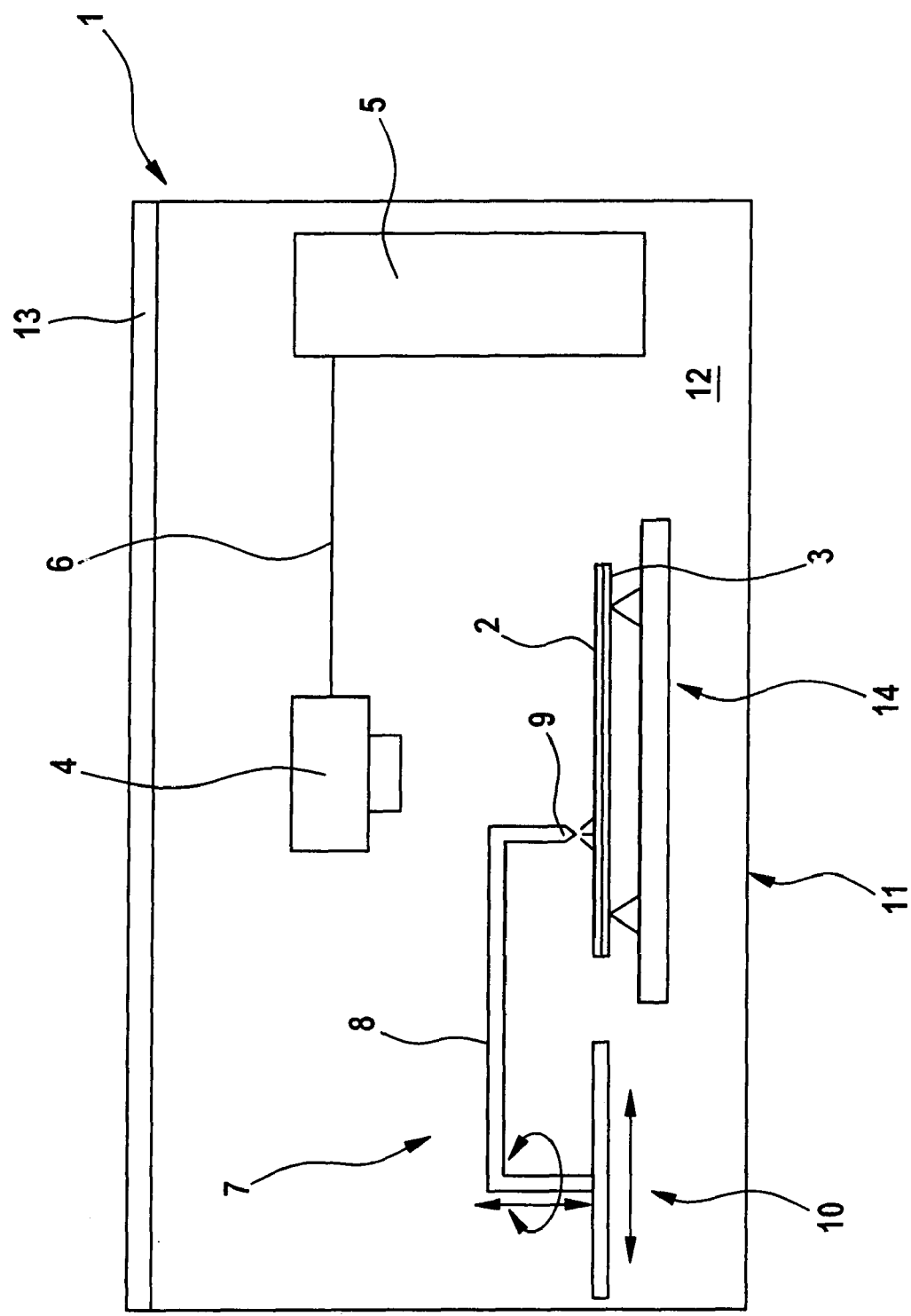
FIG. 1 shows a schematically represented lateral view onto a device for inspecting surface coatings on workpieces, in particular of lacquer coatings.

FIG. 1 accordingly shows a device 1 for inspecting surface coatings 2 on workpieces 3 or substrates 3 for ascertaining damaged spots in coating 2 and/or on element 3 to be coated. This device works without making contact on the basis of an image capture and evaluation of electromagnetic radiation, lying at least partially outside of the visible wavelength range, which is emitted by surface coating 2 and/or a layer 3 lying beneath it.

This device is suitable both for detecting irregularities or coating imperfections such as e.g. blisters, craters or dirt that exist only in coating layer 2, but it is also suitable for detecting deeper damages or layer irregularities such as popping that exist also in material 3 to be coated.

In a preferred specific embodiment, this device operates in the infrared and/or ultraviolet wavelength range. Thus in particular via the sum of the thermal radiation of the two layers, surface coating 2 and the layer of workpiece 3 lying beneath it, a comparison may be made to the thermal radiation of neighboring regions for each individual local or even for regional areas. If damage exists in the coating and/or in the connection to the surface of the workpiece beneath it, the uniform infrared radiation that is to be expected in case of a uniform coating will show a more or less clear deviation with respect to the neighboring region and will thus identify the damage. Using this inspection device it is particularly easy to detect deeper coating flaws.

For coating flaws that do not extend to the subsurface and thus do not show a clear difference in heat emission compared to neighboring regions or possibly even show no difference at all, the measurement of the change of the thermal conductivity and/or of the thermal capacity of the surface coating is provided. For this purpose, a device 7 is provided for introducing a temperature change on workpiece 3 or its surface coating 2. This device 7 may be made up e.g. of a line 8 for supplying a fluid of a different temperature than the surface coating using a nozzle 9 for a targeted discharge against surface coating 2 at a predefinable point. Furthermore, it may include a positioning device 10 having axial and rotational sliding or swiveling options for the targeted introduction of a temperature pulse at a desired location of the surface coating.

For the purpose of uniformly tempering workpiece 3 and its coating 2 that is to be inspected, device 1 includes a tempering device 11, which is here represented symbolically and schematically in the form of a chamber 12 having a heater 13. An isothermal fastening of workpiece 3 is possible via fixing device 14, which is provided for this purpose.

Figure 2:
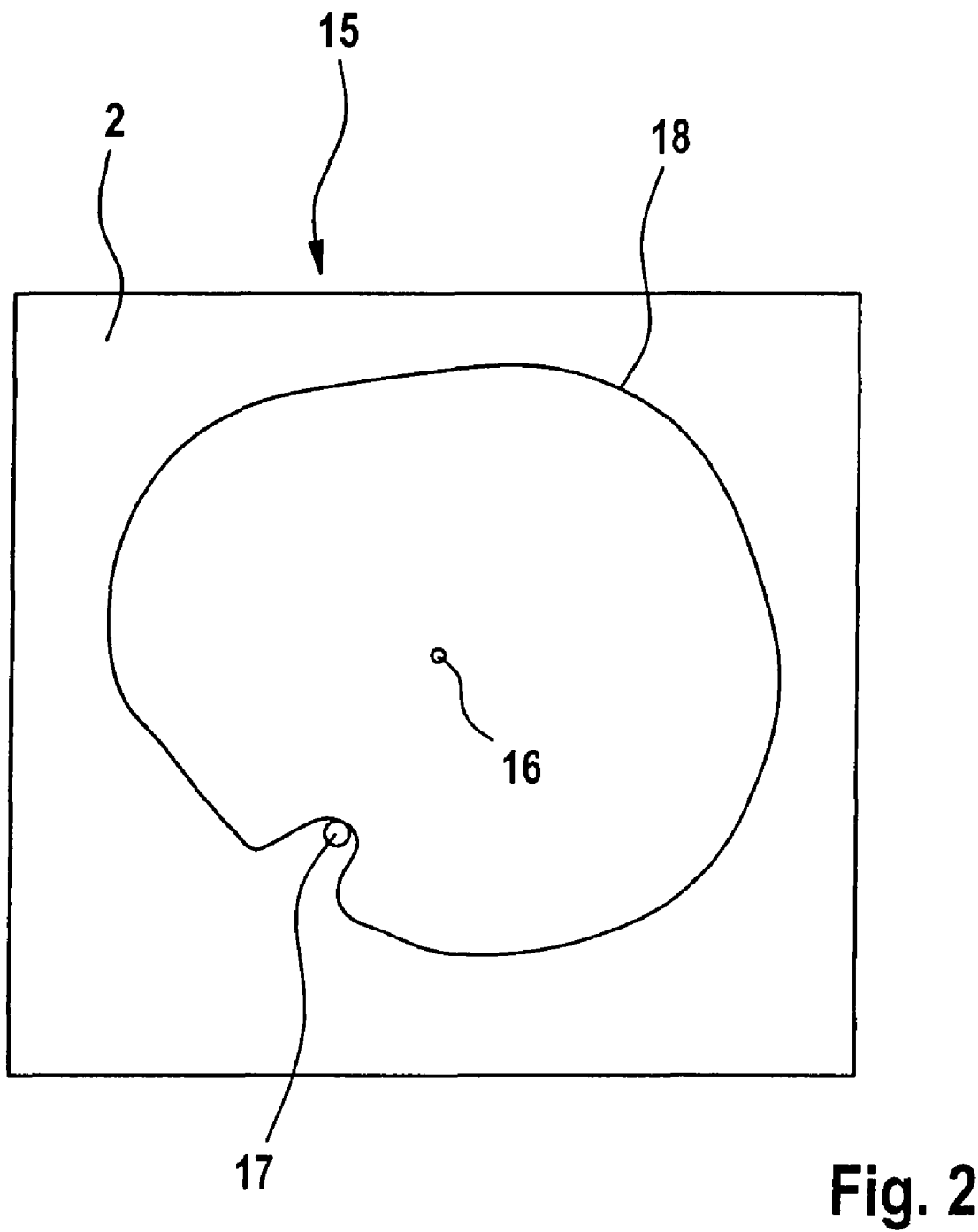
FIG. 2 shows a schematic representation of an image for inspecting a surface coating which was captured by the image capture system and which is to be processed by the image processing system.

FIG. 2 shows schematically a thermal image 15 captured by image capture system 4 and transmitted via connection 6 to image processing unit 5. This shows centrally a spray point 16, at which e.g. a cold pulse was applied to the surface of coating 2 of workpiece 3 as shown in the representation in FIG. 1. In the left lower area of the image, position 17 symbolically indicates a coating flaw, at which spreading line 18, which otherwise increases mainly in a uniform and ring-shaped manner over a certain time, is represented as temporarily retarded. The associated indentation of otherwise circular formation line 18 signals the existence of a coating flaw 17, which is detected by the comparison to previous and/or subsequent images on the part of image processing system 5 regardless of the conditions prevailing in the visible wavelength range.

What is claimed is:

1. A device for inspecting a surface coating on a workpiece, comprising:
    at least one of an image capture system and an image processing system adapted to at least one of measure and process electromagnetic radiation from at least one of the surface coating and a layer beneath the surface coating, the electromagnetic radiation being at least partly outside of the visible wavelength range;
    a first device for applying a constant temperature to the workpiece; and
    a second device for introducing a temperature change on the workpiece.

2. The device according to claim 1, wherein the surface coating is a lacquer coating.

3. The device according to claim 1, wherein the at least one of the image capture system and the image processing system works in at least one of the infrared and ultraviolet wavelength range.

4. The device according to claim 1, wherein the at least one of the image capture system and the image processing system measures at least one of a thermal conductivity and a thermal capacity of at least one of the surface coating and the layer of the workpiece beneath the surface coating.

5. The device according to claim 1, wherein the at least one of the image capture system and the image processing system measures a change of at least one of a thermal conductivity and a thermal capacity of at least one of the surface coating and the layer beneath the surface coating.

6. The device according to claim 1, wherein the at least one of the image capture system and the image processing system inspects at least one of the surface coating and the layer beneath the surface coating in a not yet cured state of the surface coating.

7. The device according to claim 1, further comprising a fixing device for producing an isothermal state for the workpiece.

8. The device according to claim 1, further comprising a device for introducing a local temperature change on the workpiece.

9. A method for inspecting a surface coating on a workpiece, comprising:
    at least one of detecting and processing, using at least one of an image capture system and an image processing system, electromagnetic radiation from at least one of the surface coating and a layer beneath the surface coating, the electromagnetic radiation being at least partially outside of the visible wavelength range;
    applying a constant temperature to the workpiece via a first device; and
    introducing a temperature change on the workpiece via a second device.

10. The method according to claim 9, wherein the surface coating is a lacquer coating.

11. The device according to claim 1, wherein the second device includes a line for supplying a fluid and a nozzle for a targeted discharge of the fuel at a desired location of the surface coating.

12. The device according to claim 11, wherein the second device further includes a positioning device capable of at least one of axial and rotational sliding and/or swiveling.

* * * * *